(12) United States Patent
Muller et al.

(10) Patent No.: US 8,877,961 B2
(45) Date of Patent: Nov. 4, 2014

(54) BRIDGED MONOBACTAM INTERMEDIATES

(71) Applicants: Marc Muller, Wolfersdorf (FR); Xiaoping Wu, Haimen (CN); Lin Xu, Shanghai (CN)

(72) Inventors: Marc Muller, Wolfersdorf (FR); Xiaoping Wu, Haimen (CN); Lin Xu, Shanghai (CN)

(73) Assignee: Basilea Pharmaceutica AG, Basel (CH)

( * ) Notice: Subject to any disclaimer, the term of this patent is extended or adjusted under 35 U.S.C. 154(b) by 28 days.

(21) Appl. No.: 13/871,338

(22) Filed: Apr. 26, 2013

(65) Prior Publication Data

US 2013/0274503 A1  Oct. 17, 2013

Related U.S. Application Data

(62) Division of application No. 12/676,580, filed as application No. PCT/EP2008/062258 on Sep. 15, 2008, now Pat. No. 8,450,477.

(30) Foreign Application Priority Data

Sep. 17, 2007 (EP) .................................... 07116603

(51) Int. Cl.
*C07C 67/36* (2006.01)
*C07D 487/04* (2006.01)
*C07C 271/22* (2006.01)
*C07C 271/54* (2006.01)

(52) U.S. Cl.
CPC ............ *C07C 271/54* (2013.01); *C07D 487/04* (2013.01); *C07C 271/22* (2013.01)
USPC ......................................................... 560/232

(58) Field of Classification Search
CPC ... C07C 271/22; C07C 271/54; C07D 487/04
USPC ..................................................... 560/24, 32
See application file for complete search history.

*Primary Examiner* — Brandon Fetterolf
*Assistant Examiner* — Blaine G Doletski

(57) ABSTRACT

C1-C6Alkyloxy- or benzyloxy-carbonyl esters of -{3-[(E)-(1-phenyl or naphthyl C1-C4alkyl)-imino]-propyl}-amino)-acetic acid, which are intermediates for producing known bridged monobactam compounds useful in the treatment of bacterial infections.

4 Claims, No Drawings

BRIDGED MONOBACTAM INTERMEDIATES

CROSS-REFERENCE TO RELATED APPLICATIONS

This Application is a divisional application of application Ser. No. 12/676,580, filed Mar. 4, 2010, which in turn is a National Stage Application of PCT/EP2008/062258, filed Sep. 15, 2008, which claims priority from European Patent Application 07116603.7 filed on Sep. 17, 2007. The priority of each prior mentioned application is claimed. Each of prior mentioned applications is hereby incorporated by reference.

The present invention relates to the manufacture of compounds of formula (I)

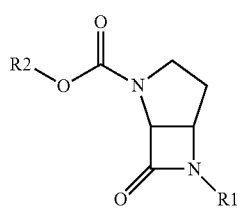

(I)

which have cis-conformation and wherein R1 and R2 have meanings defined in detail herein below, the use of said compounds as intermediates for the synthesis of pharmaceutically useful bridged monobactam compounds, like e.g. those described in EP-A-0 508 234 and WO2007/065288 which are particularly useful in the treatment of bacterial infections, certain novel intermediates of said formula (I), and a novel intermediate for the manufacture of compounds of formula (I).

Unlike other beta-lactams such as cephalosporins or penicillin, monobactams are not derived from a fermentation of a natural product but are fully synthetic compounds.

Bridged monobactams, a specific group of monobactams (cf. e.g. Heinze-Krauss et al., J. Med Chem 1998, 41, 3961-3971 and C. Hubschwerlen et al., J. Med. Chem., 1998, 41, 3972-3975), have conventionally been manufactured in a process exhibiting a large number of process steps and intermediate protection/de-protection steps, furthermore requiring the use of expensive reagents and, because of the many steps required, resulting in a rather poor overall yield. Furthermore this conventional manufacturing processes requires several chromatographic purification steps to be carried out in course of the process. The process is schematically shown in Reaction Scheme 1, and is disclosed in EP-A-0073061 and EP-A-0508234 as well as J. Med. Chem., 1998, 41, 3961-3971.

Reaction Scheme 1

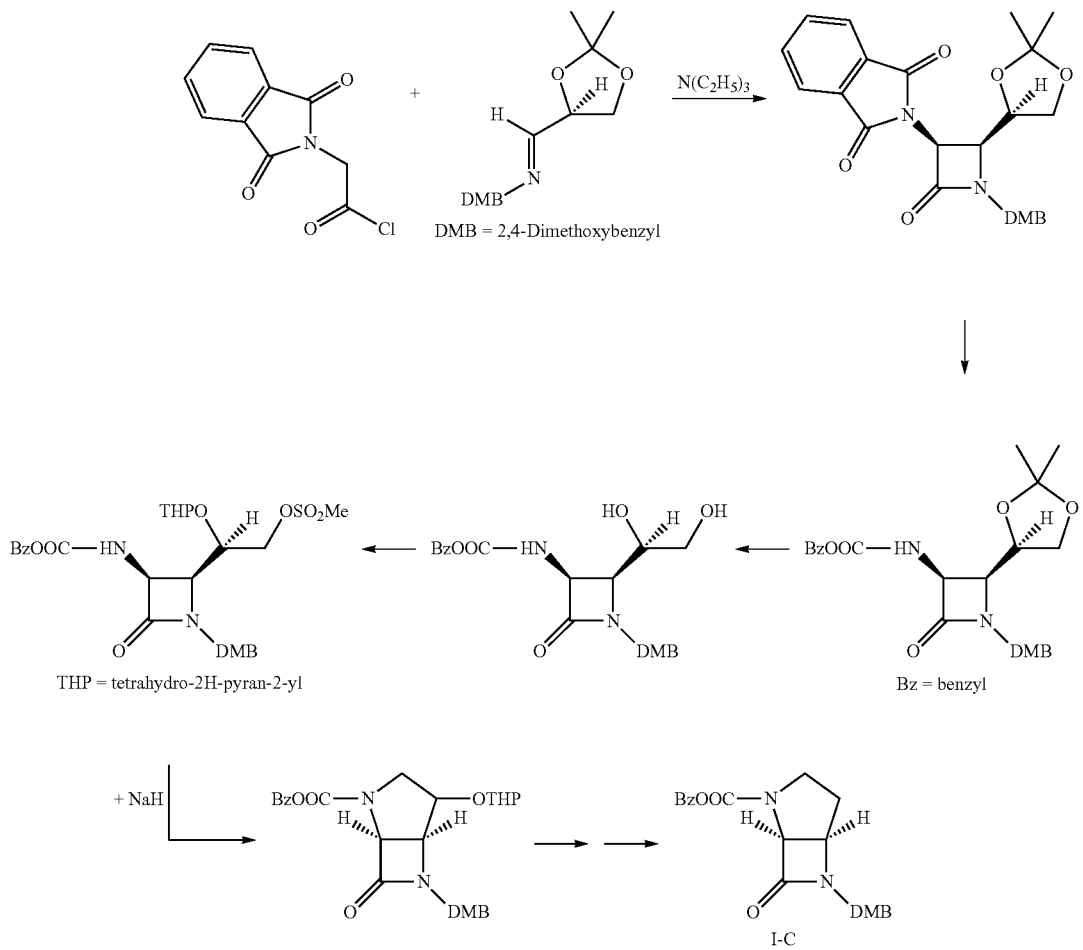

Furthermore, a stereoselective intramolecular [2+2]cycloaddition of an imine on an ortho benzylic scaffold leading to azetidino-1,2-dihydroquinazolines has been described already in prior art (cf. Journal of Organic Chemistry 2000, 65(22), 7512-7515).

The present invention is based on a new finding, namely that compounds of formula (I), including the compound of formula (I-C) mentioned in Scheme 1,

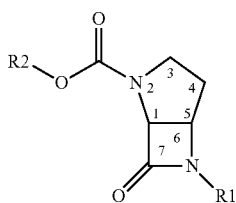

(I)

which have cis-conformation and wherein

R1 represents a 1-phenyl-$C_1$-$C_4$alkyl or 1-naphthyl-$C_1$-$C_4$alkyl group, wherein the phenyl or naphthyl moiety of R1 is unsubstituted or substituted with one or more $C_1$-$C_4$alkoxy groups and the carbon atoms in 2-, 3-, and/or 4-position of the alkyl part of R1 are, independently of the phenyl or naphthyl moiety of R1 and independently of one another, unsubstituted or substituted with $C_1$-$C_4$alkoxy and/or silyloxy, and R2 represents a $C_1$-$C_6$alkyl group or an unsubstituted or substituted benzyl group, can be prepared by treating a compound of formula (II)

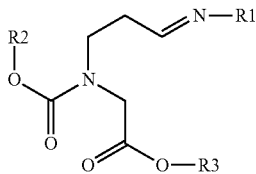

(II)

wherein

R3 represents a $C_1$-$C_6$alkyl group or an unsubstituted or substituted benzyl group, and R1 and R2 have the same meaning as in the aforementioned formula (I);

with a base at a temperature of 0° C. or less in a liquid aprotic solvent for a time period sufficient to obtain the compound of formula (I).

Without wanting to be bound to any specific mechanism of reaction, the new synthesis could formally be considered as an intramolecular [2+2]cycloaddition of the imine moiety of the compound of formula (II) with an in situ formed ketene/enolate moiety in said compound.

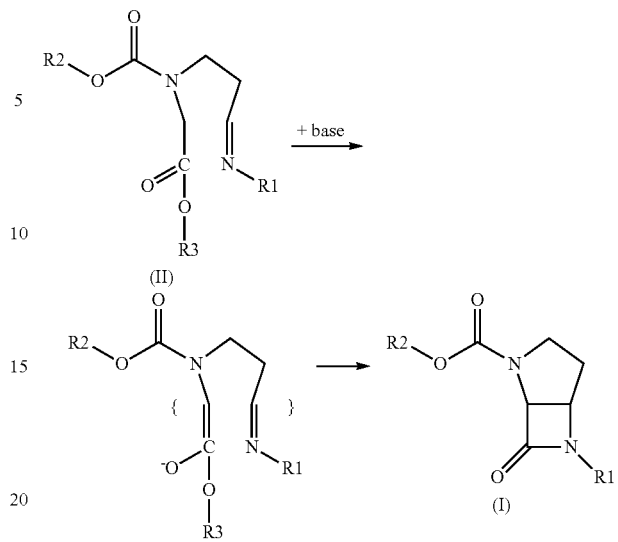

The novel synthesis provides good yields and allows the use of cheap and readily available starting materials and is, in case of chiral R1 moieties, highly stereo- and enantioselective.

In one aspect, the invention thus relates to the aforementioned process.

In a further aspect, the invention relates to a compound of formula (II)

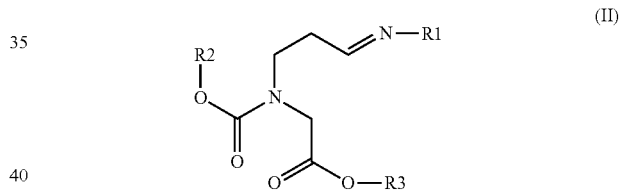

(II)

wherein

R1 represents a 1-phenyl-$C_1$-$C_4$alkyl or 1-naphthyl-$C_1$-$C_4$alkyl group, wherein the phenyl or naphthyl moiety of R1 is unsubstituted or substituted with one or more $C_1$-$C_4$alkoxy groups and the carbon atoms in 2-, 3-, and/or 4-position of the alkyl part of R1 are, independently of the phenyl or naphthyl moiety of R1 and independently of one another, unsubstituted or substituted with $C_1$-$C_4$alkoxy and/or silyloxy, and;

R2 represents a $C_1$-$C_6$alkyl group or an unsubstituted or substituted benzyl group, and R3 represents a $C_1$-$C_6$alkyl group or an unsubstituted or substituted benzyl group.

The carbon atoms in 2-, 3-, and/or 4-position of the alkyl part of R1 are preferably unsubstituted or substituted with one $C_1$-$C_4$alkoxy group and/or silyloxy group per carbon atom.

One specifically preferred embodiment of the mentioned compounds of formula (II) are compounds of formula (II-A) as defined herein below.

A further specifically preferred embodiment of the mentioned compounds of formula (II) are compounds of formula (II-B) as defined herein below.

Still a further specifically preferred embodiment of the mentioned compounds of formula (II) are compounds of formula (II-C) as defined herein below.

In yet another aspect, the invention relates to a compound selected from the still novel compounds of formula (I):

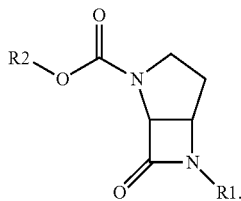

(I)

These novel compounds include specifically compounds of formula (I) having cis-conformation, wherein R1 represents a 1-phenyl-$C_2$-$C_4$alkyl or 1-naphthyl-$C_2$-$C_4$alkyl group, wherein the phenyl or naphthyl moiety of R1 is unsubstituted or substituted with one or more $C_1$-$C_4$alkoxy groups and the carbon atoms in 2-, 3-, and/or 4-position of the alkyl part of R1 are, independently of the phenyl or naphthyl moiety of R1 and independently of one another, unsubstituted or substituted with $C_1$-$C_4$alkoxy and/or silyloxy or, preferably, are unsubstituted or substituted with one $C_1$-$C_4$alkoxy group and/or silyloxy group per carbon atom, in particular a group selected from a (1S)-1-phenyl-$C_2$-$C_4$alkyl group, a (1S)-1-naphthyl-$C_2$-$C_4$alkyl group; a (1R)-1-phenyl-$C_2$-$C_4$alkyl group, and a (1R)-1-naphthyl-$C_2$-$C_4$alkyl group, most preferably (1S)-1-phenyl-ethyl and (1R)-1-phenyl-ethyl, and R2 represents a $C_1$-$C_6$alkyl group, preferably tert.-butyl, or a substituted benzyl group or more preferably an unsubstituted benzyl group.

For the purposes of this application the description of the configuration of the atom being in 1-position of the alkyl part in the 1-phenyl-$C_2$-$C_4$alkyl or 1-naphthyl-$C_2$-$C_4$alkyl groups as "(1S)" or "(1R)" ("the stereodescriptor") refers to the configuration of the respective carbon atom when said group is linked to the remainder of the molecule and when the group is not further substituted or, if it is, is considered to be not further substituted. According to the usual application of the stereodescriptors in systematic chemical nomenclature (see R. S. Cahn, C. K. Ingold and V. Prelog, *Angew. Chem. Internat. Ed. Eng.* 5, 385-415, 511 (1966); and V. Prelog and G. Helmchen, *Angew. Chem. Internat. Ed. Eng.* 21, 567-583 (1982)) the stereodescriptor may change if the 1-phenyl-$C_2$-$C_4$alkyl or 1-naphthyl-$C_2$-$C_4$alkyl group is further substituted with alkoxy or silyloxy, in particular at the carbon atom in 2-position of the alkyl part of said group, although the sterical arrangement of the atoms/groups linked to the carbon atom in 1-position does virtually not change, as shown in the following example:

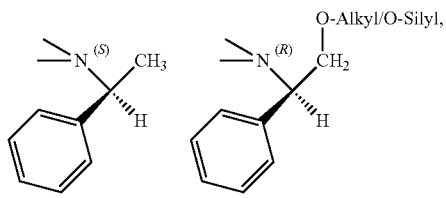

wherein N represents the nitrogen atom linked to R1 in the formulae (I) or (II). For the purposes of the present application, however, the stereodescriptors "1S" and "1R" in substituted 1-phenyl-$C_2$-$C_4$alkyl or 1-naphthyl-$C_2$-$C_4$alkyl groups R1 correspond to those of the corresponding unsubstituted 1-phenyl-$C_2$-$C_4$alkyl or 1-naphthyl-$C_2$-$C_4$alkyl groups.

Furthermore, the term "compounds of formula (I)

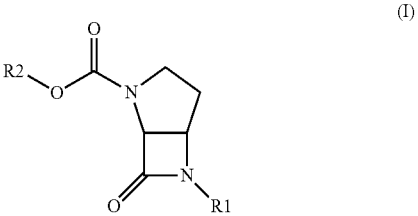

(I)

having cis-conformation" means, for the purposes of this application, in particular the compounds of the formulae (I-A), (I-B) and (I-C) indicated hereinafter.

The terms "1-phenyl-$C_1$-$C_4$alkyl" and "1-naphthyl-$C_1$-$C_4$alkyl" include e.g. benzyl; 1-phenyl-ethyl; 1-phenyl-n-propyl, and 1-phenyl-n-butyl as well as naphthyl-methyl groups, 1-naphthyl-ethyl groups; 1-naphthyl-n-propyl groups, and 1-naphthyl-n-butyl groups, including the pure or substantially pure corresponding enantiomeric forms of said residues as well as the racemic forms.

The phenyl or naphthyl moiety of R1 is unsubstituted or substituted, in particular, with one, two or more substituents, like e.g. $C_1$-$C_4$alkyl including methyl, ethyl, n-propyl, iso-propyl, n-butyl and tert-butyl; or $C_1$-$C_4$alkoxy including, in particular, methoxy and ethoxy. Preferred as substituents are one or two methyl, ethyl, methoxy and/or ethoxy substituents, most preferred one or particularly two methoxy substituents. The carbon atoms in 2-, 3-, and/or 4-position of the alkyl part of a group R1 are, independently of the phenyl or naphthyl part of R1 and independently of one another, unsubstituted or substituted with $C_1$-$C_4$alkoxy and/or silyloxy or, preferably, are unsubstituted or substituted with one $C_1$-$C_4$alkoxy group and/or silyloxy group per carbon atom, preferably with $C_1$-$C_4$alkoxy groups as defined above and/or silyloxy groups, like e.g. ($C_1$-$C_4$alkyl)$_3$SiO— groups, in particular trimethylsilyloxy or triethylsilyloxy. "Carbon atoms in 2-, 3-, and/or 4-position of the alkyl part of R1" means the carbon atoms of the $C_1$-$C_3$alkyl group indicated in the following depiction of 1-phenyl-$C_2$-$C_4$alkyl and 1-naphthyl-$C_2$-$C_4$alkyl groups as R1:

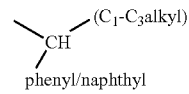

The term "1-phenyl-ethyl" includes (1S)-1-phenyl-ethyl, (1R)-1-phenyl-ethyl and racemic 1-phenyl-ethyl, i.e. a 1:1-mixture of the corresponding compounds with R1 being a (1S)-1-phenyl-ethyl group and the corresponding compounds with R1 being a (1R)-1-phenyl-ethyl group.

Benzyl and particularly 2,4-dimethoxybenzyl and 3,4-dimethoxybenzyl, as well as 1-phenyl-ethyl are especially preferred as groups R1.

The term "$C_1$-$C_6$alkyl group" in the definition of R2 and R3 includes corresponding straight and branched alkyl groups, like those already mentioned above or e.g. n-pentyl, isopentyl or n-hexyl. An alkyl group R2 is preferably tert.-butyl, an alkyl group R3 is preferably ethyl.

The meaning "unsubstituted or substituted benzyl group" for R2 includes particularly benzyl itself and benzyl groups, wherein the phenyl moiety of the benzyl group is substituted by one, two or three $C_1$-$C_4$alkyl groups as defined above or $C_1$-$C_4$alkoxy groups as defined above.

The meaning "unsubstituted or substituted benzyl group" for R3 includes particularly benzyl itself and benzyl substituted by one, two or three $C_1$-$C_4$alkyl groups as defined above or $C_1$-$C_4$alkoxy groups as defined above.

Specific embodiments of the processes according to the present invention include in particular:

a process for manufacturing a compound of formula (I), wherein said compound is selected from the compounds of formula (I-A)

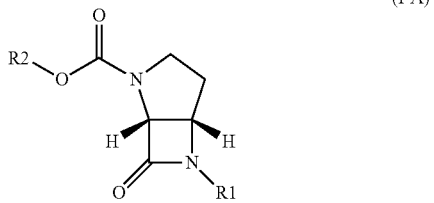

(I-A)

wherein

R1 represents a (1S)-1-phenyl-$C_2$-$C_4$alkyl or a (1S)-1-naphthyl-$C_2$-$C_4$alkyl group, wherein the phenyl or naphthyl moiety of R1 is unsubstituted or substituted with one or more $C_1$-$C_4$alkoxy groups and the carbon atoms in 2-, 3-, and/or 4-position of the alkyl part of R1 are, independently of the phenyl or naphthyl moiety of R1 and independently of one another, unsubstituted or substituted with $C_1$-$C_4$alkoxy and/or silyloxy or, preferably, are unsubstituted or substituted with one $C_1$-$C_4$alkoxy group and/or silyloxy group per carbon atom, and R2 has the meaning already mentioned above, in which process a compound of formula (II-A)

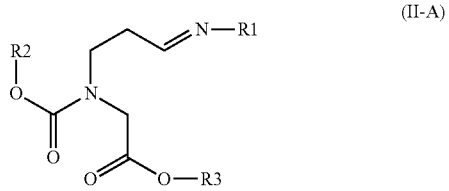

(II-A)

wherein

R1 has the same meaning as in formula (I-A); and

R2 and R3 have the meaning already mentioned above;

is treated with a base at a temperature of 0° C. or less in a liquid aprotic solvent for a time period sufficient to obtain the compound of formula (I-A);

a process for manufacturing a compound of formula (I), wherein said compound is selected from the compounds of formula (I-B)

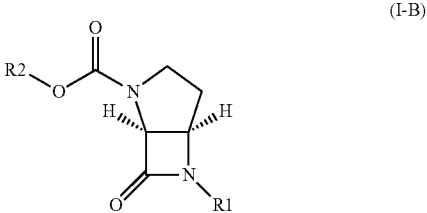

(I-B)

wherein

R1 represents a (1R) 1-phenyl-$C_2$-$C_4$alkyl or a (1R)-1-naphthyl-$C_2$-$C_4$alkyl group, wherein the phenyl or naphthyl moiety of R1 is unsubstituted or substituted with one or more $C_1$-$C_4$alkoxy groups and the carbon atoms in 2-, 3-, and/or 4-position of the alkyl part of R1 are, independently of the phenyl or naphthyl moiety of R1 and independently of one another, unsubstituted or substituted with $C_1$-$C_4$alkoxy and/or silyloxy or, preferably, are unsubstituted or substituted with one $C_1$-$C_4$alkoxy group and/or silyloxy group per carbon atom, and R2 has the meaning already mentioned above, in which process a compound of formula (II-B)

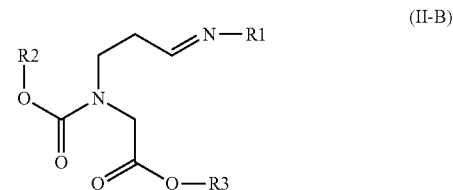

(II-B)

wherein

R1 has the same meaning as in formula (I-B); and

R2 and R3 have the meaning already mentioned above;

is treated with a base at a temperature of 0° C. or less in a liquid aprotic solvent for a time period sufficient to obtain the compound of formula (I-B); and a process for manufacturing a compound of formula (I), wherein said compound is selected from the racemates (I-C) of compounds of formula (I)

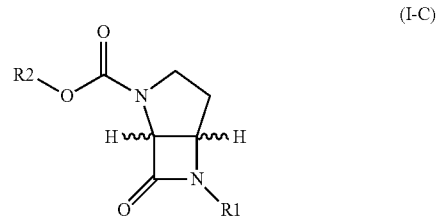

(I-C)

which has cis-conformation and wherein

R1 represents a benzyl or naphthylmethyl group or a racemic 1-phenyl-$C_2$-$C_4$alkyl or a 1-naphthyl-$C_2$-$C_4$alkyl group, wherein the phenyl or naphthyl moiety of R1 is unsubstituted or substituted with one or more $C_1$-$C_4$alkoxy groups and the carbon atoms in 2-, 3-, and/or 4-position of the alkyl part of R1 are, independently of the phenyl or naphthyl moiety of R1 and independently of one another, unsubstituted or substituted with $C_1$-$C_4$alkoxy and/or silyloxy or, preferably, are unsubstituted or substituted with one $C_1$-$C_4$alkoxy group and/or silyloxy group per carbon atom, and R2 has the meaning already mentioned above,
in which process a compound of formula (II-C)

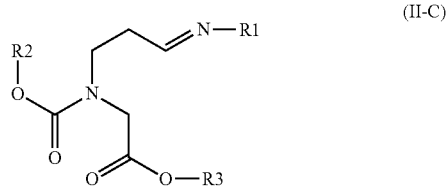

(II-C)

wherein
R1 has the same meaning as in formula (I-C); and
R2 and R3 have the meaning already mentioned;
is treated with a base at a temperature of 0° C. or less in a liquid aprotic solvent for a time period sufficient to obtain the compound of formula (I-C).

The base used in the aforementioned processes is preferably selected from NaH; lithium diisopropylamide (LDA); lithium-, sodium- or potassium-hexamethyldisilazide (LiHMDS; NaHMDS; KHMDS); 1,5-diazabicyclo[4.3.0]non-5-ene (DBN) and 1,8-diazabicyclo[5.4.0]undec-7-ene (DBU). In certain cases it may also be appropriate to use mixtures of bases like those mentioned. Preferred bases are lithium diisopropylamide (LDA) and, more particularly, lithium-hexamethyldisilazide (LiHMDS).

The reaction of the compound of formula (II) with the base in the aforementioned processes is, in general, carried out at a temperature of about 0° C. or less, e.g. at temperatures from minus 78° C. to 0° C. More preferably the reaction is carried out at about minus 78° C. to minus 50° C., in particular minus 78° C. to minus 70° C.

The aprotic solvent used for this process must be liquid at the reaction temperature. The solvent is preferably selected from diethylether; tetrahydrofurane (THF); tert.-butylmethyether (TBME); petrol ether; liquid alkanes with up to 8 carbon atoms, liquid cycloalkanes with up to 8 carbon atoms, benzene or a benzene substituted by one or more $C_1$-$C_4$alkyl groups like e.g. toluene, xylenes or mesitylenes or mixtures thereof.

Suitable reaction times range preferably from 1 to 20 hours, more particularly 3 to 12 hours, e.g. 5 to 10 hours. Longer reaction times are also within the scope of the present invention. One can e.g. keep the reaction mixture, optionally with stirring, for some further hours, e.g. 1 to 10 hours at about room temperature, although this is normally not necessary because the reaction is sufficiently fast.

Preferred embodiments of the processes described above include process variants wherein one or more of the following conditions and particularly all said conditions, apply:
the base is selected from lithium diisopropylamide (LDA) and lithium-hexamethyl-disilazide (LiHMDS);
the temperature is minus 78° C. to minus 70° C.;
the solvent is tetrahydrofurane (THF); and/or
the reaction time is 1 to 12 hours.

In another preferred aspect, it is preferred to apply the above-mentioned processes to a compound of formula (II) wherein
R1 is selected from (1S)-1-phenyl-ethyl, (1R)-1-phenylethyl, racemic 1-phenyl-ethyl, 2,4-dimethoxybenzyl and 3,4-dimethoxybenzyl;
R2 is selected from tert.-butyl and benzyl, and R3 is selected from $C_1$-$C_4$alkyl groups, in particular ethyl, and benzyl.

The compound of formula (II) can e.g. be obtained by reacting a compound of formula (III) with a primary amine of formula (IV)

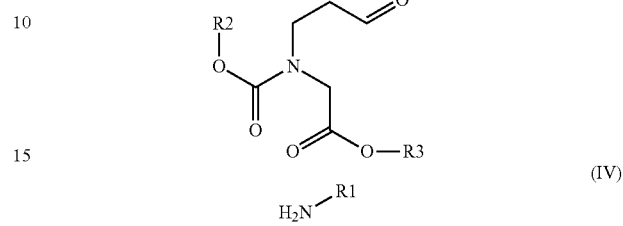

in which formulae R1, R2 and R3 have any one of the meanings defined above.

In said process the compound of formula (III) is reacted with the primary amine of formula (IV) at temperatures generally ranging from minus 20° C. to 80° C. in a liquid aprotic solvent, either in the presence of a desiccating agent or with azeotropic removal of the water formed in said process under reduced pressure.

More preferably, one or more of the following conditions and particularly all said process conditions, are used in said process:
the reaction temperature is about room temperature, that means e.g. 10° C. to 35° C., preferably 20° C. to 30° C.;
the solvent is selected from tert.-butylmethylether (TBME), diethyl-ether, tetrahydrofurane (THF), methylene chloride, dioxane, $C_5$-$C_7$alkanes, $C_5$-$C_7$cycloalkanes, benzene or benzenes substituted by one or more $C_1$-$C_4$alkyl groups, formamide, dimethylformamide (DMF), 1,3-Dimethyl-3,4,5,6-tetrahydro-2(1H)-pyrimidinone (DMPU); and/or
the desiccating agent is selected from anhydrous magnesium sulfate, anhydrous sodium sulfate and molecular sieves or, more preferably, the water formed in said process is azeotropically removed under reduced pressure.

In an especially preferred embodiment of the process for manufacturing the compound of formula (III), the use of a reaction temperature of 20° C. to 30° C. is combined with an azeotropic removal of the water formed in said process under reduced pressure.

The compounds of formula (III) can advantageously be obtained e.g. from the corresponding alcohols of formula (V)

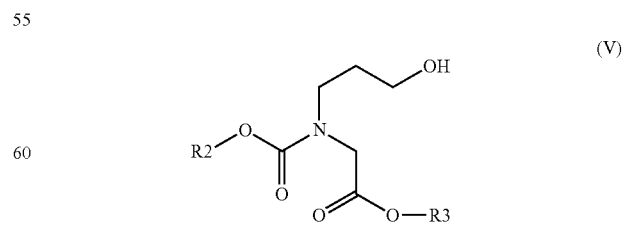

wherein R2 and R3 have the same meaning as in formula (III), by conventional known alcohol oxidation methods (such as the Swern oxidation).

The compounds of formula (V) in turn can be obtained by reaction of the corresponding amino-alcohols of formula (VI)

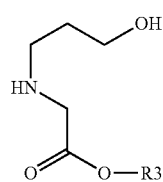
(VI)

wherein R3 has the same meaning as in formula (V) with the corresponding carbonates, chloroformates or anhydrides.

The compounds of formula (VI) can e.g. be obtained by reacting 3-amino-propanol with the corresponding halo-acetic acid esters (cf. e.g. Tetrahedron Letters; 1988; 29(18); 2195-2196).

It is also an advantage of the process for manufacturing a compound of formula (I) according to the present invention that the compound of formula (II) can be used without previous purification when it has been obtained according to the process described herein.

The compounds of formula (I) can e.g. be further processed to yield compounds of formula (A)

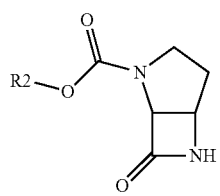
(A)

which have cis-conformation and wherein
R2 has the same meaning as for the compound of formula (I).

Depending on the residue R1 of the compound of formula (I) used in said reaction, different methods can be applied for said reaction.

In particular, if R1 in formula (I) is selected from 2,4-dimethoxybenzyl and 3,4-dimethoxybenzyl, the compound of formula (I) is advantageously converted to the compound of formula (A) by reacting it with a peroxosulfate or a peroxodisulfate salt in a solvent like e.g. acetonitrile, acetonitrile/water and the like. This reaction is described in more detail e.g. in J. Med Chem 1998, 41, 3961-3971, in particular 3968.

Preferably Oxone® is chosen as the peroxosulfate or a peroxodisulfate salt for the aforementioned reaction, which is a commercially available salt of the composition: $2KHSO_5 \cdot KHSO_4 \cdot K_2SO_4$.

If R1 in formula (I) is a 1-phenyl-$C_2$-$C_4$alkyl or 1-naphthyl-$C_2$-$C_4$alkyl group, in particular such a group selected from (1S)-1-phenyl-ethyl, (1-R)-1-phenyl-ethyl and racemic 1-phenyl-ethyl, the compound of formula (I) is advantageously converted to the compound of formula (A) by reacting it with an alkali metal selected from lithium, potassium and preferably sodium in liquid ammonia in the presence of a $C_1$-$C_4$alcohol. This reaction is known as BIRCH reduction (cf. e.g. R. C. Richards; Tetrahedron Letters; 1989; 30(39); 5239.5242).

Preferably, the compound of formula (I) is reacted with metallic sodium in liquid ammonia at a temperature of about minus 78° C. in said BIRCH reduction. Reaction times range from about 30 minutes to a few hours, e.g. 30 minutes to 3 hours.

The compounds of formula (A) can also be further processed to yield a derivative thereof like e.g. a corresponding 6-sulfonic acid compound or a salt thereof, preferably a corresponding β-lactamase inhibitor compound, like, in particular, (1S,5R)-2-[N-(4-{[(2-amino-ethyl)amino]carbonylamino}phenyl)aminocarbonyl]-7-oxo-2,6-diaza-bicylo[3.2.0]heptane-6-sulfonic acid or a salt thereof. The process is generally shown in the following Reaction Scheme 2, wherein Py SO₃ stands for the pyridine sulfur trioxide complex, Py means pyridine and TFA trifluoroacetic acid.

Reaction Scheme 2

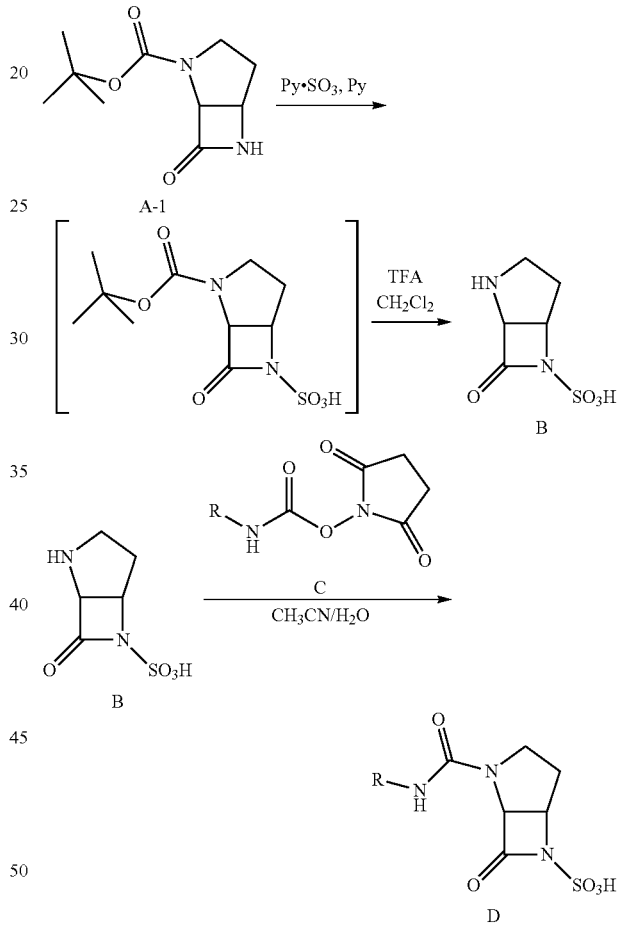

The sulfonation of Compound A-1 followed by removal of the BOC protecting group generates compound B and can e.g. be accomplished as described (J. Med. Chem. 1998, 3961 and J. Org. Chem. 1982, 5160).

If R2 in the compound of formula (A) represents an unsubstituted or substituted benzyl group, it may e.g. be first hydrogenated in presence of BOC₂O to afford the intermediate compound A-1 of Reaction Scheme 2. This is described e.g. in Tetrahedron Lett. 1988, 2983.

Compound B may then be reacted with the appropriate succinimidyl derivative C to yield a desired compound D. Suitable succinimidyl derivatives C may be synthesized and introduced according to the procedures described in J. Med.

Chem. 1998, 3961. Suitable examples of groups R are described in the prior art, e.g. in EP-A-0 508 234, WO2007/065288 etc.

(1S,5R)-2-[N-(4-{[(2-amino-ethyl)amino]carbonylamino}phenyl)aminocarbonyl]-7-oxo-2,6-diaza-bicyclo[3.2.0]heptane-6-sulfonic acid is exemplified as compound 324 in WO2007/065288 and its pharmaceutical usefulness is demonstrated therein with biological data. The present invention therefore also relates to a process as described above wherein a compound of formula (I) is further processed to yield a derivative thereof, a corresponding 6-sulfonic acid compound or a salt thereof, in particular a β-lactamase inhibitor compound like, in particular, (1S,5R)-2-[N-(4-{[(2-amino-ethyl)amino]carbonylamino}phenyl)aminocarbonyl]-7-oxo-2,6-diaza-bicyclo[3.2.0]heptane-6-sulfonic acid or a salt thereof.

EXAMPLE 1

(3-Hydroxy-propylamino)-acetic acid ethyl ester

3-Aminopropan-1-ol (154 g; 2.05 mol) is cooled to −5° C. Ethyl bromoacetate (143.6 g; 817 mmol) is added dropwise over a period of 1.5 hours maintaining the temperature around 5-10° C. The stirring is continued for 10 minutes. LC-MS showed that all ethyl bromoactetate has reacted. Then water (570 ml) is added to the reaction mixture. The aqueous mixture is washed three times with ethylacetate (3 times 140 ml). The combined organic phases are back extracted with water (2 times 140 ml). The aqueous phases are combined and saturated with sodium chloride (255 g). The aqueous solution is extracted with methylene chloride (6 times 750 ml). The combined organic phases are dried over sodium sulfate and the solvent is removed under reduced pressure. A yellow oil is obtained (83 g; yield 63%)

NMR: ($CDCl_3$; 400 MHz): 4.15 (q; J=7.2 Hz; 2H); 3.75 (t; J=5.6 Hz; 2H); 3.36 (s; 2H); 3.03 (s(br); 2H; OH and NH); 2.80 (t; J=5.6 Hz; 2H); 1.68 (quint.; J=5.6 Hz; 2H); 1.22 (t; J=7.2 Hz; 3H).

EXAMPLE 2

2-[(tert-Butyloxycarbonyl)-(3-hydroxy-propyl)-amino]-acetic acid ethyl ester (3-Hydroxy-propylamino)-acetic acid ethyl ester (83 g; 0.515 mol) is dissolved in methylene chloride (240 ml) at 2-5° C. BOC anhydride (112.5 g; 0.514 mol) is added slowly. The mixture is stirred at 2-5° C. for one hour. LC-MS indicated that all starting material has reacted. The solvent is removed under reduced pressure at 30° C. A yellow oil is obtained (157 g; quantitative yield)

NMR: ($CDCl_3$; 400 MHz): 4.16 (q; J=7.2 Hz; 2H); 4.01 and 3.92 and 3.82 (2s; 2H); 3.63 (t; J=5.6 Hz; 2H); 3.49 and 3.42 (2t; J=5.6 Hz; 2H); 1.74 and 1.63 (2quint.; J=5.6 Hz; 2H); 1.45 and 1.40 (2s; 9H); 1.24 (t; J=7.2 Hz; 3H).

EXAMPLE 3

2-[(tert-Butyloxycarbonyl)-(3-oxo-propyl)-amino]-acetic acid ethyl ester

Oxalyl chloride (131.5 g; 1.03 mol) is dissolved in methylene chloride (680 ml). The mixture is cooled to −74° C. (internal temperature) and DMSO (110 ml; 1.54 mol) is added dropwise. The mixture is stirred for 30 minutes, then a solution of tert-butyloxycarbonyl-(3-hydroxy-propyl)amino]-acetic acid ethyl ester (157 g; 0.515 mol) in methylene chloride (340 ml) is added dropwise over a period of 20 minutes. The mixture is stirred for 25 minutes, then triethylamine (384 ml; 2.75 mol) is added over a period of 25 minutes. The mixture is stirred for 45 minutes, LC-MS indicated that all alcohol has reacted at −78° C. The reaction allowed to warm to room temperature and is quenched with a 1.5M aqueous KH2PO4 solution (1.7 L). The phases are separated. The aqueous phase is extracted twice with methylene chloride (2 times 400 ml). The organic phases are combined and washed three times with water and subsequently once with brine. The organic phase is dried over sodium sulfate and the solvent is removed under reduced pressure. A yellow oil is obtained (150 g; yield quantitative).

NMR: ($CDCl_3$; 400 MHz): 9.82 (s; 1H); 4.21 (q; J=7.2 Hz; 2H); 4.02 and 3.96 (2s; 2H); 3.60 (m; 2H); 2.86 and 2.80 (m; 2H); 1.49 and 1.43 (2s; 9H) 1.28 (m; 3H).

EXAMPLE 4

2-{tert-Butyloxycarbonyl-[3-(1(R)-phenyl-ethylimino)-propyl]-amino}-acetic acid ethyl ester tert-Butyloxycarbonyl-(3-oxo-propyl)-amino]-acetic acid ethyl ester (59.7 g; 0.23 mol) is dissolved in cyclohexane (600 ml). (R)-1-Methylbenzylamine (26.5 g; 0.218 mol) is added at 10-13° C. The mixture is stirred for 20 minutes and the solvent is removed under reduced pressure (azeotropical removal of water). The oily residue (99 g; yield quantitative) is directly used in the next step.

NMR: (DMSO; 400 MHz): 7.81 (m; 1H); 7.34-7.11 (m; 5H); 4.27 (m; 1H); 4.09 (m; 1H); 3.93 and 3.90 (2s; 2H); 3.45 (m; 1H); 1-39-1.29 (m; 11H); 1.21-1.17 (m; 6H)

EXAMPLE 5

(1S,5R)-7-Oxo-6-(1(R)-phenyl-ethyl)-2,6-diaza-bicyclo[3.2.0]heptane-2-carboxylic acid tert-butyl ester {tertButyloxycarbonyl-[3-(1(R)-phenyl-ethylimino)-propyl]-amino}-acetic acid ethyl ester (99 g; 0.23 mol) is dissolved in dry THF (420 ml). The mixture is cooled to −74° C. and a LiHMDS solution in THF (219 ml of a 1M solution) is added drop wise over a period of 1 hour. The cold reaction mixture (−74° C.) is added in an aqueous 1.5M KH2PO4 solution (820 ml). THF is removed under reduced pressure keeping the bath temperature below 28° C. The aqueous mixture is extracted three times with ethyl acetate. The combined organic phases are washed with water and brine and dried over sodium sulfate. The solvent is removed under reduced pressure and a crude yellow oil is obtained (68.7 g). This oil is dissolved in methylene chloride and filtered through a small silicagel pad (33 g; about 3 cm thickness) using methylene chloride as eluent. 61.4 g of an orange crude oil is obtained. This oil is dissolved in a heptane/ethyl acetate mixture (136 ml; 12/1) at room temperature and the desired compound is allowed to precipitate at 0° C. over a period of 2 days. A yellow solid is obtained (10.7 g; yield: 14.6%)

NMR: ($CDCl_3$; 400 MHz): 7.38-7.28 (m; 5H); 5.12 (s(broad); 0.4H); 4.92 (s(broad); 0.6H) 4.83 (q; J=7.2; 1H);

4.08 (m(br); 1H); 3.94 (m(br); 1H); 3.21 (td; 1H); 1.82 (m; 1H); 1.64 (d; J=7.2; 3H); 1.57(m;1H); 1.47 (s; 9H).

EXAMPLE 6

(1S,5R)-7-Oxo-2,6-diaza-bicyclo[3.2.0]heptane-2-carboxylic acid tert-butyl ester Ammonia (ca 100 ml) is condensed in a 4-necked flask at −78° C. Pieces of sodium metal (2.3 g; 0.1 mol) are added. The reaction mixture is stirred at −78° C. for one hour. The reaction mixture turned to deep blue. Then (1S,5R)-7-oxo-6-(1(R)-phenyl-ethyl)-2,6-diaza-bicyclo[3.2.0]heptane-2-carboxylic acid tert-butyl ester (10.57 g; 33.4 mmol) dissolved in dry THF (40 ml) and dry tert-butanol (4.4 ml) is added dropwise at this temperature. LC/MS analysis indicates that 2 minutes after the end of the addition the reaction is complete. The reaction is quenched by addition of solid ammonium chloride (10.56 g) and stirred for additional 30 minutes at −78° C. The reaction turns colorless. The excess of ammonia is evaporated and the residue is dissolved in 1.5M aqueous KH2PO4 solution (95 ml). The mixture is extracted three times with ethylacetate. The combined organic phases are washed with brine and dried over sodium sulfate. The solvent is removed under reduced pressure at 30° C. and the residue is dissolved in a methanol/water mixture (48 ml MeOH and 80 ml of water). This aqueous phase is washed three times with heptane. Methanol is removed under reduced pressure at 35° C. and the aqueous phase is extracted three times with ethylacetate. The combined organic phases are washed with brine and dried over sodium sulfate. The solvent is removed and 5.51 g of crude product is obtained. The crude solid is dissolved in ethyl acetate (17 ml) at reflux and heptane (32 ml) is added. The mixture is cooled at 0° C. and the product is allowed to crystallize over night. The crystals are filtered off, washed with heptane and dried. Colorless crystals are obtained (4.46 g; yield 62.9%).

NMR: (CDCl$_3$; 400 MHz): 5.76 (s(br); 1H; NH); 5.15 and 5.09 (2s(broad); 1H); 4.30 (s(br); 1H); 4.04 (s(br); 1H); 3.33 (td; J=11.6, 6.1; 1H); 1.95 (dd; J=13.8, 6.1; 1H); 1.76 (m; 1H); 1.48 (s; 9H).

Chiral HPLC: ee>99.5%, Absolute configuration confirmed by chiral HPLC (column: Daicel AD-H) comparison with an authentic sample prepared according to Hubschwerlen et al, J. Med. Chem., 1998, 41, 3972-3975

Synthesis of the enantiomer: (1R,5S)-7-Oxo-2,6-diaza-bicyclo[3.2.0]heptane-2-carboxylic acid tert-butyl ester

EXAMPLE 4'

2-{tert-Butyloxycarbonyl-[3-(1(S)-phenyl-ethylimino)-propyl]-amino}-acetic acid ethyl ester tert-Butyloxycarbonyl-(3-oxo-propyl)-amino]-acetic acid ethyl ester (28 g; 0.108 mol) is dissolved in THF (200 ml). (S)-1-Methylbenzylamine (13.7 g; 0.108 mol) is added at 15° C. Molecular sieves (4 angström; 14 g) are added to the reaction mixture and this mixture is stirred at 15° C. for 2 hours. This mixture is directly used in the next step.

EXAMPLE 5'

(1R,5S)-7-Oxo-6-(1(S)-phenyl-ethyl)-2,6-diaza-bicyclo[3.2.0]heptane-2-carboxylic acid tert-butyl ester The previous mixture is cooled to −78° C. and a LiHMDS solution in THF (107 ml of a 1M solution) is added drop wise over a period of 1 hour. The cold reaction mixture (−78° C.) is added in an aqueous 1.5M KH2PO4 solution (350 ml). THF is removed under reduced pressure keeping the bath temperature below 28° C. The aqueous mixture is extracted three times with ethyl acetate. The combined organic phases are washed with water and brine and dried over sodium sulfate. The solvent is removed under reduced pressure and a crude yellow oil is obtained (31.3 g). This oil is dissolved in a hexane/ethyl acetate mixture (215 ml; 40/3) at 60° C. and the desired compound is allowed to precipitate at 5° C. over a period of 3 days. A yellow solid is obtained (11.5 g; yield: 33.8%; HPLC purity: 92.4%; de: 97.2%)

NMR: (CDCl$_3$; 400 MHz): 7.38-7.28 (m; 5H); 5.12 (s(broad); 0.4H); 4.92 (s(broad); 0.6H) 4.83 (q; J=7.2; 1H); 4.08 (m(br); 1H); 3.94 (m(br); 1H); 3.21 (td; 1H); 1.82 (m; 1H); 1.64 (d; J=7.2; 3H); 1.57(m;1H); 1.47 (s; 9H).

EXAMPLE 6'

(1R,5S)-7-Oxo-2,6-diaza-bicyclo[3.2.0]heptane-2-carboxylic acid tert-butyl ester Ammonia (ca 100 ml) is condensed in a 4-necked flask at −78° C. Pieces of sodium metal (4.1 g; 0.178 mol) are added. The reaction mixture is stirred at −78° C. for one hour. The reaction mixture turns to deep blue. Then (1R,5S)-7-oxo-6-(1(S)-phenyl-ethyl)-2,6-diaza-bicyclo[3.2.0]heptane-2-carboxylic acid tert-butyl ester (10.57 g; 33.4 mmol) dissolved in dry THF (100 ml) and dry tert-butanol (0.5 ml) is added dropwise at this temperature. LC/MS analysis indicates that 2 minutes after the end of the addition the reaction is complete. The reaction is quenched by addition of solid ammonium chloride (10.56 g) and stirred for additional 30 minutes at −78° C. The reaction turns colorless. The excess of ammonia is evaporated and the residue is dissolved in saturated ammonium chloride solution (200 ml). The mixture is extracted three times with ethylacetate. The combined organic phases are washed with brine and dried over sodium sulfate. The solvent is removed under reduced pressure at 30° C. and the residue is dissolved in a methanol/water mixture (50 ml MeOH and 100 ml of water). This aqueous phase is washed three times with hexanes. Methanol is removed under reduced pressure at 35° C. and the aqueous phase is extracted three times with ethylacetate. The combined organic phases are washed with brine and dried over sodium sulfate. The solvent is removed and 4 g of crude product is obtained. The crude solid is dissolved in ethyl acetate (21 ml) at reflux and hexane (100 ml) is added. The mixture is cooled at 0° C. and the product is allowed to crystallize over night. The crystals are filtered, washed with heptane and dried. Colorless crystals are obtained (2.4 g; yield 31.3%; HPLC purity: 98.8%; Chiral HPLC ee: 99.45%).

NMR: (CDCl$_3$; 400 MHz): 5.76 (s(br); 1H; NH); 5.15 and 5.09 (2s(broad); 1H); 4.30 (s(br); 1H); 4.04 (s(br); 1H); 3.33 (td; J=11.6, 6.1; 1H); 1.95 (dd; J=13.8, 6.1; 1H); 1.76 (m; 1H); 1.48 (s; 9H).

EXAMPLE 7

2-[(Benzyloxycarbonyl)-(3-hydroxy-propyl)-amino]-acetic acid ethyl ester

A cooled (5° C.) aqueous solution (750 ml) of (3-hydroxy-propylamino)-acetic acid ethyl ester, sodium bicarbonate (125 g; 1.49 mol) is added. After 30 minutes, benzyl chloroformate (63.5 g: 372 mmol) is added slowly. The mixture is stirred 2 hours at 5° C. Then ethyl acetate (1000 ml) is added to the mixture. The phases are separated. The aqueous phase is extracted twice with ethyl acetate (2 times 500 ml). The combined organic phases are washed twice with water (2 times 500 ml) and with brine (500 ml). The organic phase is dried over magnesium sulfate. The solids are filtered off and the solvent is removed under reduced pressure. Impurities contained in the crude product (benzyl alcohol mainly) are removed by distillation at reduced pressure. 57.5 g of a light yellow oil (yield 82.4%; based on bromo ethyl acetate; see Example 1) are obtained.

NMR: (CDCl$_3$; 400 MHz): 7.36-7.29 (m; 5H); 5.15 and 5.13 (2s; 2H); 4.21 and 4.11 (2q; J=7.2 Hz; 2H); 4.01 and 3.94 (2s; 2H); 3.63 (t; J=5.6 Hz; 2H); 3.50 and 3.45 (2t; J=5.6 Hz; 2H); 2.41 (s(br); 1H; NH); 1.74 and 1.69 (2quint.; J=5.6 Hz; 2H); 1.28 and 1.19 (2t; J=7.2 Hz; 3H).

EXAMPLE 8

2-[(Benzyloxycarbonyl)-(3-oxo-propyl)-amino]-acetic acid ethyl ester

Benzyloxycarbonyl-(3-hydroxy-propyl)-amino]-acetic acid ethyl ester (10 g; 33.9 mmol) is dissolved in DMSO (60 ml). Triethylamine (30 ml; 215 mmol) is added. Then sulfur trioxide pyridine complex (16.2 g; 102 mmol) dissolved in DMSO (60 ml) is added at 14° C. and the mixture is stirred for 3.5 hours. Aqueous hydrochloric acid solution (2M) is added till the pH reached a value of 5 while keeping the temperature at 14° C. Then the reaction mixture is extracted with ethyl acetate (3 times 200 ml). The combined organic phases are washed twice with aqueous HCl (0.5 M solution; 2 times 200 ml) and with brine (200 ml). The organic layer is dried over anhydrous sodium sulfate. The solids are filtered off and the solvent is removed under reduced pressure. The aldehyde is obtained as a yellow oil (9.4 g; yield 94.6%).

NMR: (CDCl$_3$; 400 MHz): 9.79 and 9.73 (2s; 1H); 7.36-7.26 (m; 5H); 5.15 and 5.10 (2s; 2H); 4.17 and 4.12 (2q; J=7.2 Hz; 2H); 4.07 and 4.03 (2s; 2H); 3.63 (m; 2H); 2.86 and 2.80 (2t; J=5.6 Hz; 2H); 1.26 and 1.18 (2t; J=7.2 Hz; 3H).

EXAMPLE 9

[(1R,5S), (1S,5R) 1:1]-6-(2,4-Dimethoxy-benzyl)-7-oxo-2,6-diaza-bicyclo[3.2.0]heptane-2-carboxylic acid benzyl ester 2-[(Benzyloxycarbonyl)-(3-oxo-propyl)-amino]-acetic acid ethyl ester (0.25 g; 0.85 mmol)) is dissolved in dichloromethane (10 ml). Anhydrous magnesium sulfate (1 g) is added. The reaction mixture is cooled to 0° C. and 2,4-dimethoxy-benzylamine (0.143 g; 0.85 mmol) is added and the mixture is stirred at 0° C. for 4 hours. The solids are filtered off and the solvent is removed under reduced pressure. 0.35 g of a colorless oil (yield 93 (Y0) is obtained. The obtained imine is directly used in the next step.

The imine (0.175 g; 0.4 mmol) is dissolved in dry THF (10 ml). The reaction mixture is cooled to −78° C. and LDA (0.24 ml of a 2M solution in THF) is added slowly. The reaction mixture is stirred 10 hours at −78° C., then the reaction mixture is warmed to room temperature and stirred overnight. The reaction mixture is then poured in chilled water and extracted with ethyl acetate; the phases are separated. The aqueous phase is extracted twice with ethyl acetate (2 times 10 ml). The combined organic phases are washed with water (10 ml) and with brine twice (2 times 10 ml). The organic phase is dried over sodium sulfate. The solids are filtered off and the solvent is removed under reduced pressure. The crude product is purified by column chromatography over silicagel (eluent: hexane/ethyl acetate 10:1). 0.045 g of a colorless waxy solid (yield 33%) are obtained.

IR: (film; in cm$^{-1}$): 3013; 2920; 2848; 1753; 1703; 1614; 1589; 1508; 1421; 1294; 1209; 1157; 1035; 756; 698; 667.

EXAMPLE 10

2-{Benzyloxycarbonyl-[3-(1(R)-phenyl-ethylimino)-propyl]-amino}-acetic acid ethyl ester 2[(Benzyloxycarbonyl)-(3-oxo-propyl)-amino]-acetic acid ethyl ester (0.32 g; 1.09 mmol)) is dissolved in dichloromethane (10 ml). Molecular sieves (2 g; 3 Angström) are added. The reaction mixture is cooled to 0° C. and (R)-(+)-1-phenylethylamine (0.132 g; 1.09 mmol) is added and the mixture is stirred at 0° C. for 4 hours. The solids are filtered off and the solvent is removed under reduced pressure. 0.35 g of a light yellow oil (yield 93%) is obtained. The obtained imine is directly used in the next step.

EXAMPLE 11

(1S,5R)-7-Oxo-6-(1(R)-phenyl-ethyl)-2,6-diaza-bicyclo[3.2.0]heptane-2-carboxylic acid benzyl ester 2-{Benzyloxycarbonyl-[3-(1(R)-phenyl-ethylimino)-propyl]-amino}-acetic acid ethyl ester (0.909 g; 2.29 mmol) is dissolved in dry THF (20 ml). The reaction mixture is cooled to −78° C. and LDA (1.6 ml of a 2M solution in THF) is added slowly. The reaction mixture is stirred for 6 hours at −78° C. Then, the reaction mixture is poured in chilled saturated aqueous ammonium chloride solution and extracted with ethyl acetate; the phases are separated. The aqueous phase is extracted twice with ethyl acetate (2 times 100 ml). The combined organic phases are washed with water (50 ml) and with brine twice (2 times 50 ml). The organic phase is dried over magnesium sulfate. The solids are filtered off and the solvent is removed under reduced pressure. The crude product is purified by column chromatography over silicagel (eluent: hexane/ethyl acetate 50:1 to 10:1). 0.418 g of a colorless yellow oil (yield 52%) are obtained.

NMR: (CDCl$_3$; 400 MHz): 7.38-7.28 (m; 10H); 5.12 (d(AB broad); 2H); 5.02 (m; 1H); 4.83 (q; J=7.2; 1H); 4.12-3.90 (m; 2H); 3.29 (m; 1H); 1.85 (m; 1H); 1.66 (d; J=7.2; 3H); 1.57 (m; 1H).

EXAMPLE 12

(1S,5R)-7-Oxo-6-(1(R)-phenyl-ethyl)-2,6-diaza-bicyclo[3.2.0]heptane-2-carboxylic acid tert-butyl ester (1S,5R)-7-Oxo-6-(1(R)-phenyl-ethyl)-2,6-diaza-bicyclo[3.2.0]heptane-2-carboxylic acid benzyl ester (500 mg; 1.43 mmol) is dissolved in ethanol (20 ml). Palladium on charcoal (5%; 150 mg) is added to the reaction mixture. Then BOC anhydride (370 mg; 1.71 mmol) is added. The reaction mixture is stirred under hydrogen atmosphere at a pressure of 1 bar for 4 hours. The palladium catalyst is filtered off.

The solvent is removed under reduced pressure. The crude product is purified by column chromatography over silicagel (eluent: Hexane/Ethyl acetate 10:1). 0.3 g of a white semi-solid (yield 66.5%) are obtained.

NMR: (CDCl$_3$; 400 MHz): 7.38-7.28 (m; 5H); 5.12 (s(broad); 0.4H); 4.92 (s(broad); 0.6H) 4.83 (q; J=7.2; 1H);

4.08 (m(br); 1H); 3.94 (m(br); 1H); 3.21 (td; 1H); 1.82 (m; 1H); 1.64 (d; J=7.2; 3H); 1.57(m;1H); 1.47 (s; 9H).

EXAMPLE 13

This example illustrates the further processing of the intermediates according to the present invention by the example of converting the product of Example 6 of the present application to Compound 324 disclosed in WO2007/065288, i.e. to (1S,5R)-2-[N-(4-{[(2-aminoethyl)amino]carbonylamino}phenyl)carbamoyl]-7-oxo-2,6-diazabicyclo[3.2.0]heptane-6-sulfonic acid (see also Reaction Scheme 2)

(a) Preparation of (1S,5R)-7-oxo-2,6-diazabicyclo[3.2.0]heptane-6-sulfonic acid (Compound B according to Reaction Scheme 2):

A solution of (1S,5R)-7-Oxo-2,6-diaza-bicyclo[3.2.0]heptane-2-carboxylic acid tert-butyl ester (Compound A-1 according to Reaction Scheme 2) obtained according to Example 6 of the present application (10.00 g, 47.11 mmol, 1.0 eq) in pyridine (90 mL) is heated at 80° C. before the addition of $Py.SO_3$ (22.64 g, 141.34 mmol, 3.0 eq). The reaction mixture is stirred at 80° C. for 1 h30, then poured into aqueous 0.5 M $KH_2PO_4$ (100 mL). The aqueous solution is then extracted twice with $CH_2Cl_2$ (2×100 mL) and the resulting combined organic layers are back-extracted with an additional phosphate solution (100 mL).

Treatment of the combined aqueous phases with tetrabutylammonium hydrogen sulfate (16.00 g, 47.11 mmol, 1.0 eq) followed by extraction with $CH_2Cl_2$ (3×200 mL) and drying over $Na_2SO_4$ gives after concentration the expected intermediate. This intermediate is dissolved in $CH_2Cl_2$ (240 mL) and TFA (18.15 mL, 235.57 mmol, 5.0 eq) is added at 0° C. in order to remove the BOC protecting group. The resulting mixture is allowed to warm to room temperature. After 24 hours stirring at room temperature additional TFA (18.15 mL, 235.57 mmol, 5.0 eq) is added. After stirring at room temperature for an additional 24 hours, the reaction mixture is filtered to afford the expected Compound B as a white powder: 8.00 g (84%)

NMR (DMSO-d6): 1.75 (m, 1H); 2.45 (dd, J=5.8 and 14.2, 1H); 3.07 (m, 1H); 3.62 (m, 1H); 4.43 (t, J=4.2, 1H); 4.89 (d, J=3.8, 1H); 9.50 (br, 2H).

(b) Preparation of (tert-butoxy)-N-{4-[(fluoren-9-ylmethoxy)carbonylamino]phenyl}carboxamide Triethylamine (7.36 mL, 52.82 mmol, 1.1 eq) is added at 0° C. to a stirred solution of N—BOC-1,4-phenylene diamine (10.00 g, 48.02 mmol, 1.0 eq) in $CH_3CN$ (240 mL), followed by 9-fluorenylmethyloxycarbonyl chloride (14.90 g, 57.62 mmol, 1.2 eq). The resulting mixture is allowed to warm to room temperature. After 4 hours stirring at room temperature, the reaction mixture is filtered to afford 20.60 g of the crude product as a white powder which is used in the next step without any further purification.

1H-NMR (DMSO-$d_6$): 1.46 (s, 9H); 4.29 (t, J=6.6, 1H); 4.44 (d, J=6.3, 2H); 7.30-7.45 (m, 8H); 7.75 (d, J=7.4, 2H); 7.91 (d, J=7.4, 2H); 9.22 (br, 1H); 9.59 (br, 1H).

(c) Preparation of N-(4-aminophenyl)(fluoren-9-ylmethoxy)carboxamide

TFA (55.30 mL, 717.76 mmol, 15.0 eq) is added at 0° C. to a stirred solution of (tert-butoxy)-N-{4-[(fluoren-9-ylmethoxy)carbonylamino]phenyl}carboxamide (20.60 g, 47.85 mmol, 1.0 eq) in $CH_2Cl_2$ (900 mL). The resulting solution is allowed to warm to room temperature. After stirring overnight at room temperature, the reaction mixture is concentrated to dryness and the residue is triturated in water. Then the mixture is filtered to afford 15.80 g of the expected crude product as a white powder.

1H-NMR (DMSO-$d_6$): 4.30 (t, J=6.4, 1H); 4.49 (d, J=6.4, 2H); 7.06 (d, J=7.7, 2H); 7.40 (m, 6H); 7.74 (d, J=7.4, 2H); 7.91 (d, J=7.4, 2H); 8.95 (br, 2H); 9.73 (br, 1H).

(d) Preparation of N-{4-[(2,5-dioxoazolidinyloxy)carbonylamino]phenyl}(fluoren-9-ylmethoxy)carboxamide N,N'-Disuccinimidylcarbonate (16.20 g, 63.26 mmol, 1.1 eq) is added at room temperature to a stirred solution of N-(4-aminophenyl)(fluoren-9-ylmethoxy)carboxamide (20.00 g, 60.53 mmol, 1.0 eq) in $CH_3CN$ (1100 mL). After stirring overnight at room temperature, the reaction mixture is filtered to afford 28.50 g of the expected crude product as a white powder.

1H-NMR (DMSO-$d_6$): 2.83 (br, 4H); 4.31 (t, J=6.4, 1H); 4.48 (m, 2H); 7.20-7.50 (m, 8H); 7.5 (d, J=7.4, 2H); 7.91 (d, J=7.4, 2H); 9.72 (br, 1H); 10.67 (br, 1H).

(e) Preparation of N-{4-[({2-[(tert-butoxy)carbonylamino]ethyl}amino)-carbonylamino]phenyl}(fluoren-9-ylmethoxy)carboxamide A solution of N-{4-[(2,5-dioxoazolidinyloxy)carbonylamino]phenyl}(fluoren-9-ylmethoxy)carboxamide (16.10 g, 34.15 mmol, 1.0 eq) in $H_2O/CH_3CN$ (1/1, v/v, 360 mL) is reacted at room temperature with $NaHCO_3$ (2.86 g, 34.15 mmol, 1.0 eq) and N—BOC-ethylenediamine (5.47 g, 34.15 mmol, 1.0 eq). After stirring overnight at room temperature, the reaction mixture is filtered to afford 16.36 g of the expected crude product as a white solid.

1H-NMR (DMSO-$d_6$): 1.37 (s, 9H); 2.98 (m, 2H); 3.11 (m, 2H); 4.29 (t, J=6.4, 1H); 4.44 (d, J=6.4, 2H); 6.10 (m, 1H); 6.85 (m, 1H); 7.30-7.50 (m, 8H); 7.74 (d, J=7.4, 2H); 7.90 (d, J=7.4, 2H); 8.40 (s, 1H); 9.53 (br, 1H).

(f) Preparation of N-(4-aminophenyl)({2-[(tert-butoxy)carbonylamino]ethyl}amino) carboxamide Piperidine (9.68 mL, 97.75 mmol, 5.0 eq) is added at room temperature to a stirred solution of N-{4-[({2-[(tert-butoxy)carbonylamino]ethyl}amino)carbonylamino]-phenyl}(fluoren-9-ylmethoxy)carboxamide (10.10 g, 19.55 mmol, 1.0 eq) in DMF (140 mL). After 2 hours stirring at room temperature, water is added to the reaction mixture and precipitation occurred. The resulting mixture is filtered, and the liquid phase is concentrated to afford 6.75 g of the expected product as an orange oil:

1H-NMR (DMSO-$d_6$): 1.37 (s, 9H); 2.98 (m, 2H); 3.11 (m, 2H); 4.69 (s, 2H); 6.00 (t, J=5.5, 1H); 6.44 (d, J=8.6, 2H); 6.81 (t, J=5.3, 1H); 6.97 (d, J=8.6, 2H); 8.00 (s, 1H).

(g) Preparation of ({2-[(tert-butoxy)carbonylamino]ethyl}amino)-N-{4-[(2,5-dioxoazolidinyloxy)carbonylamino]phenyl}carboxamide N,N'-Disuccinimidylcarbonate (5.49 g, 21.44 mmol, 1.1 eq) is added at room temperature to a stirred solution of N-(4-aminophenyl)({2-[(tert-butoxy)carbonyl-amino] ethyl}amino)carboxamide (6.75 g, 19.49 mmol, 1.0 eq) in CH$_3$CN (350 mL).

After stirring overnight at room temperature, the reaction mixture is filtered to afford 9.70 g of the expected crude product as a light brown solid.

$^1$H-NMR (DMSO-d$_6$): 1.37 (s, 9H); 2.82 (br, 4H); 2.99 (m, 2H); 3.11 (m, 2H); 6.12 (t, J=5.2, 1H); 6.85 (t, J=5.5, 1H); 7.27 (d, J=8.9, 2H); 7.36 (d, J=8.9, 2H); 7.95 (s, 1H); 8.53 (s, 1H).

(h) Preparation of [(2-aminoethyl)amino]-N-{4-[(2, 5-dioxoazolidinyloxy)carbonylamino] phenyl}carboxamide (Compound C-1)

TFA (11.59 mL, 150.54 mmol, 5.0 eq) is added at room temperature to a stirred suspension of ({2-[(tert-butoxy)carbonylamino]ethyl}amino)-N-{4-[(2,5-dioxoazolidinyloxy) carbonylamino]phenyl}carboxamide (13.8 g, 30.11 mmol, 1.0 eq) in CH$_2$Cl$_2$ (165 mL). After stirring overnight at room temperature, solvent is evaporated and the crude product is triturated with Et$_2$O to afford 14.2 g of the expected crude product as a beige solid and as the trifluoroacetic acid salt.

1H-NMR (DMSO-d$_6$): 2.82 (br, 4H); 2.88 (m, 2H); 3.30 (m, 2H); 6.51 (t, J=5.6, 1H); 7.30 (d, J=8.9, 2H); 7.40 (d, J=8.9, 2H); 7.77 (br, 3H); 8.85 (s, 1H); 10.61 (s, 1H).

(i) Preparation of (1S,5R)-2-[N-(4-{[(2-aminoethyl) amino]carbonylamino}phenyl)carbamoyl]-7-oxo-2, 6-diazabicyclo[3.2.0]heptane-6-sulfonic acid (Compound D-1)

(1S,5R)-7-oxo-2,6-diazabicyclo[3.2.0]heptane-6-sulfonic acid (Compound B of Reaction Scheme 2, 2.0 g, 10.41 mmol, 1.0 eq) is dissolved in H$_2$O (12.5 mL). Then CH$_3$CN (100 mL) is added at room temperature to the solution, followed by NaHCO$_3$ (1.57 g, 18.73 mmol, 1.8 eq) and [(2-aminoethyl) amino]-N-{4-[(2,5-dioxoazolidinyloxy)carbonylamino] phenyl}carboxamide (Compound C-1) (6.89 g, 14.57 mmol, 1.4 eq). After stirring overnight at room temperature, the reaction mixture is filtered to afford 3.27 g of the expected (1S,5R)-2-[N-(4-{[(2-aminoethyl)amino] carbonylamino}phenyl)carbamoyl]-7-oxo-2,6-diazabicyclo [3.2.0]heptane-6-sulfonic acid as a white solid.

1H-NMR (DMSO-d$_6$): 1.65 (m, 1H); 2.30 (dd, J=5.8 and 13.5, 1H); 2.90 (m, 2H); 3.18 (m, 1H); 3.30 (m, 2H); 3.98 (m, 1H); 4.41 (t, J=4.7, 1H); 5.22 (d, J=4.3, 1H); 6.23 (t, J=5.7, 1H); 7.28 (d, J=8.2, 2H); 7.33 (d, J=8.2, 2H); 7.65 (br, 3H); 8.38 (s, 1H); 8.53 (s, 1H).

We claim:
1. A compound of formula (II)

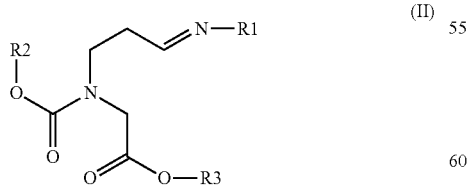

(II)

wherein
R1 represents a 1-phenyl-C$_1$-C$_4$alkyl or 1-naphthyl-C$_1$-C$_4$alkyl group, wherein the phenyl or naphthyl moiety of R1 is unsubstituted or substituted with one or more C$_1$-C$_4$alkoxy groups and the carbon atoms in 2-, 3-, and/or 4-position of the alkyl part of R1 are, independently of the phenyl or naphthyl moiety of R1 and independently of one another, unsubstituted or substituted with C$_1$-C$_4$alkoxy and/or silyloxy or are unsubstituted or substituted with one C$_1$-C$_4$alkoxy group and/or silyloxy group per carbon atom;

R2 represents a C$_1$-C$_6$alkyl group or an unsubstituted or substituted benzyl group, and R3 represents a C$_1$-C$_6$alkyl group or an unsubstituted or substituted benzyl group.

2. The compound of claim 1 having the formula (II-A)

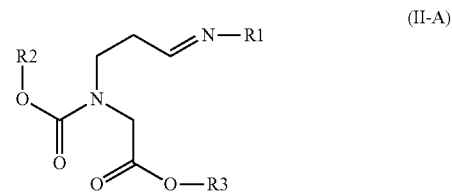

(II-A)

wherein
R1 represents a (1S)-1-phenyl-C$_2$-C$_4$alkyl or a (1S)-1-naphthyl-C$_2$-C$_4$alkyl group, wherein the phenyl or naphthyl moiety of R1 is unsubstituted or substituted with one or more C$_1$-C$_4$alkoxy groups and the carbon atoms in 2-, 3-, and/or 4-position of the alkyl part of R1 are, independently of the phenyl or naphthyl moiety of R1 and independently of one another, unsubstituted or substituted with C$_1$-C$_4$alkoxy and/or silyloxy, or are unsubstituted or substituted with one C1C4alkoxy group and/ or silyloxy group per carbon atom, and R2 represents a C$_1$-C$_6$alkyl group or an unsubstituted or substituted benzyl group; and R3 represents a C$_1$-C$_6$alkyl group or an unsubstituted or substituted benzyl group.

3. The compound of claim 1 having the formula (II-B)

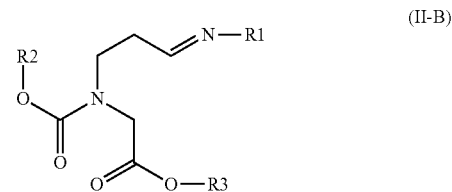

(II-B)

wherein
represents a (1R)-1-phenyl-C$_2$-C$_4$alkyl or a (1R)-1-naphthyl-C$_2$-C$_4$alkyl group, wherein the phenyl or naphthyl moiety of R1 is unsubstituted or substituted with one or more C$_1$-C$_4$alkoxy groups and the carbon atoms in 2-, 3-, and/or 4-position of the alkyl part of R1 are, independently of the phenyl or naphthyl moiety of R1 and independently of one another, unsubstituted or substituted with C$_1$-C$_4$alkoxy and/or silyloxy, or are unsubstituted or substituted with one C1C4alkoxy group and/or silyloxy group per carbon atom, and R2 represents a C$_1$-C$_6$alkyl group or an unsubstituted or substituted benzyl group; and R3 represents a C$_1$-C$_6$alkyl group or an unsubstituted or substituted benzyl group.

4. The compound of claim 1 having the formula (II-C)

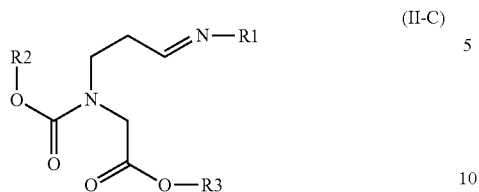

wherein
- R1 represents a benzyl or naphthylmethyl group or a racemic 1-phenyl-$C_2$-$C_4$alkyl or a 1-naphthyl-$C_2$-$C_4$allyl group, wherein the phenyl or naphthyl moiety of R1 is unsubstituted or substituted with one or more $C_1$-$C_4$alkoxy groups and the carbon atoms in 2-, 3-, and/or 4-position of the alkyl part of R1 are, independently of the phenyl or naphthyl moiety of R1 and independently of one another, unsubstituted or substituted with $C_1$-$C_4$alkoxy and/or silyloxy, or are unsubstituted or substituted with one C1C4alkoxy group and/or silyloxy group per carbon atom, and
- R2 represents a $C_1$-$C_6$alkyl group or an unsubstituted or substituted benzyl group; and
- R3 represents a $C_1$-$C_6$alkyl group or an unsubstituted or substituted benzyl group.

* * * * *